United States Patent
Jährling

(10) Patent No.: US 7,257,849 B2
(45) Date of Patent: Aug. 21, 2007

(54) ADAPTER TO ATTACH A PATIENT POSITIONING PLATE OF A PATIENT TRANSPORT CART TO A DIAGNOSIS AND/OR TREATMENT TABLE, IN PARTICULAR OF A MEDICAL EXAMINATION MODALITY

(75) Inventor: Peter Jährling, Puschendorf (DE)

(73) Assignee: Siemens Aktiengesellschaft, Munich (DE)

( * ) Notice: Subject to any disclaimer, the term of this patent is extended or adjusted under 35 U.S.C. 154(b) by 117 days.

(21) Appl. No.: 10/834,829

(22) Filed: Apr. 29, 2004

(65) Prior Publication Data

US 2004/0262870 A1    Dec. 30, 2004

(30) Foreign Application Priority Data

Apr. 29, 2003   (DE)   ................. 103 19 307

(51) Int. Cl.
*A61B 6/04*    (2006.01)
(52) U.S. Cl. ........................................ 5/81.1 R; 5/601

(58) Field of Classification Search .................... 5/600, 5/601, 607, 609, 81.1 R
See application file for complete search history.

(56) References Cited

U.S. PATENT DOCUMENTS

| 3,167,789 | A | * | 2/1965 | Wicks ..................... 5/81.1 HS |
| 3,947,686 | A | * | 3/1976 | Cooper et al. .............. 378/209 |
| 4,819,925 | A | * | 4/1989 | Linnemann et al. ........... 5/606 |
| 4,905,267 | A | * | 2/1990 | Miller et al. ................ 378/208 |
| 6,560,799 | B1 | | 5/2003 | Pflaum et al. |
| 6,862,761 | B2 | * | 3/2005 | Hand et al. .................... 5/600 |

* cited by examiner

*Primary Examiner*—Patricia Engle
*Assistant Examiner*—Fredrick Conley
(74) *Attorney, Agent, or Firm*—Schiff Hardin LLP

(57) ABSTRACT

Adapter for attaching a patient positioning plate of a patient transport cart or gurney to a diagnosis and/or treatment table, in particular of a medical examination modality, has attachment elements for detachable attachment to the diagnosis and/or treatment table, and the shape of the top side of the adapter in the attachment region for the patient positioning plate is substantially adapted to the underside of the patient positioning plate.

13 Claims, 2 Drawing Sheets

ADAPTER TO ATTACH A PATIENT POSITIONING PLATE OF A PATIENT TRANSPORT CART TO A DIAGNOSIS AND/OR TREATMENT TABLE, IN PARTICULAR OF A MEDICAL EXAMINATION MODALITY

BACKGROUND OF THE INVENTION

1. Field of the Invention

The present invention concerns an adapter to attach a patient positioning plate of a patient transport gurney or cart to a diagnosis and/or treatment table, in particular of a medical examination modality.

2. Description of the Prior Art

The transfer of recumbent patients (that naturally thus have only limited movement) from the patient transport cart to a diagnosis and/or treatment table is very work- and time-intensive. Normally a number of people, often up to six, are necessary for the transfer, since the patient that is manually transferred must be kept very stable in order to prevent the patient from suffering injury during the transfer. In the transfer, the patient is shifted from the patient positioning table of a patient transport cart (gurney) to the diagnosis and/or treatment table, or is raised using a sheet or a board. A single transfer is already difficult, and an even greater effort exists when a patient must be transferred multiple times. A transfer normally takes at least five minutes, thus if six people are required, a transfer involves a total effort of a half work-hour, For patients who must be frequently transferred due to back illnesses, for example, or for trauma patients, the transfer frequently entails a total effort of a number of work-hours. This is very involved and finally also very cost-intensive. Moreover, the transfer event is laborious for the people undertaking it, since it ensues (as stated) manually and a considerable must be lifted, and this must often ensue very slowly and carefully.

SUMMARY OF THE INVENTION

An object of the present invention is to provide an adaptor that allows attachment of a patient positioning plate of a patient transport cart to a diagnosis and/or treatment table in a more simple manner than as heretofore been possible.

This object is achieved in accordance with the invention by an adapter of the type initially described that allows a patient positioning plate of a patient transport cart that can be removed from this or slid under this to be attached to a diagnosis and/or treatment table, in particular of a medical examination modality, for example an x-ray system, a magnetic resonance device, an operating table or the like, such that the patient is not moved manually. For this purpose, the inventive adapter is provided with an attachment element for detachable attachment to the diagnosis and/or treatment table, and the shape of the top of the adapter in the attachment area for the patient positioning plate substantially corresponds to the bottom of the patient positioning plate and for allowing the patient positioning plate to be coupled with the adapter substantially without slippage.

Due to the top side adaptation, with regard to shape or dimensioning, to the bottom side of the patient positioning plate, the inventive adapter enables it to be securely accepted. The shape is in particular selected or adapted such that the patient positioning plate cannot slide relative to the adapter, at least in a direction transverse to the longitudinal axis of the table. Via the attachment element, the adapter can be detachably attached to the diagnosis and/or treatment table, which is normally narrower than the patient positioning plate is wide. A secure attachment of the patient positioning plate to the diagnosis and/or treatment table can thus be achieved with particular advantage with the adapter. In operation, the patient is transported with the patient transport cart to the examination modality, and is positioned next to the diagnosis and/or treatment table. After attachment of the adapter or adapters to the diagnosis and/or treatment table, the patient positioning plate is carried to the diagnosis and/or treatment table, by being lifted over it or pulled out laterally relative to the patient positioning cart. The patient positioning plate subsequently is lowered and placed on the adapter. Depending on the embodiment, the patient transport cart now can be removed, or can remain standing nearby. In any case, apart from the manual lifting and placement of the patient positioning plate, which normally can ensue with two persons, further manual handling that would be laborious and time-consuming is no longer necessary. In this manner, as a result of the coupling realized with the adapter to make use of the patient positioning plate, which is present anyway, in the framework of the subsequent diagnosis or treatment, the patient is not to be transferred from this plate. The previously cited difficulties are avoided with particular advantage. The labor associated with the conventional procedure can be used elsewhere and the overall treatment costs can be kept lower because less work time is incurred for transfers.

In an embodiment of the invention, the shape or size of the underside of the adapter in the attachment region at the diagnosis and/or treatment table substantially corresponds to the shape of the abutting surface of the diagnosis and/or treatment apparatus. Diagnosis and/or treatment tables normally are not planar, but Instead are frequently fashioned somewhat trough-shaped. In order to now achieve a secure placement of the adapter on the diagnosis and/or treatment table (which is important so that a secure and position-precise mounting of the patient positioning plate is possible relative to the diagnosis and/or treatment table), the underside of the adapter is largely adapted to the shape of the table top, insofar as the adapter lies thereon. Thus a sufficiently large and secure positioning surface is achieved. Because tables of different manufacturers are frequently very similar with regard to their trough shape, with an adapter it is by all means possible to be able to securely attach a patient positioning plate to various diagnosis and/or treatment tables, even of different manufacturers or types.

In order to prevent that the patient positioning plate from sliding relative to the adapter, it is appropriate for the width of the adapter in the attachment region to the patient positioning plate to be dimensioned such that any projections of the patient positioning plate that are provided laterally on the underside overlap with the adapter on the edges with little play (clearance; free motion). On a patient positioning table of a patient transport cart, insofar as the plate can be removed or laterally slid, projections at the edges normally are provided that are used in connection with the inventive adapter to keep it from sliding. The width of the adapter is thereby dimensioned such that it is directly accepted between the projections with little play, so that the plate cannot slide in a direction transverse to its longitudinal axis relative to the adapter. Thus, if the doctor or an aide unintentionally bumps against the patient positioning plate during the treatment, there is no danger since the plate cannot slide.

In an exemplary embodiment, the attachment element for connection with the diagnosis and/or treatment table is Velcro® strips or Velcro® pads. At the top of the majority of the diagnosis and/or treatment tables, Velcro® strips or Velcro® pads are provided that allow attachment of overlays such as fabric covers, water-impermeable covers and the like that have corresponding Velcro® strips or Velcro® pads. These attachment elements existing at the table are advantageously used in connection with the inventive adapter, by providing corresponding Velcro® attachment elements on the adapter that are correspondingly positioned such that they come into direct contact, with the Velcro® elements at the table upon placement of the adapter on the diagnosis and/or treatment table. A simple and quick attachment of the adapter to the table thus is achieved. As an alternative to Velcro® attachment elements, or in addition to them, the attachment elements can be a plug, a catch or a clamp. If in the form of a clamp, for example, clamp arms or the like can be arranged laterally on the adapter that overlap the table edge on both sides and are fixed on the underside of the table. Plugs or catches are also suitable that can be engaged in corresponding recesses on the table.

In another exemplary embodiment, the adapter itself can be fashioned substantially planar on the top side and curved on the underside. The flat top side allows a simple acceptance of the patient positioning plate, the curved underside allows for the typical trough-shape of the table. This exemplary embodiment can be formed as a two-part arrangement of an upper plate part and a formed component attached to its bottom. The formed component itself can be formed from a shaped rigid foam as a deformed plate that is connected with the upper plate part. For example, a formed part made of plastic or a fiber-reinforced plastic, preferably a carbon fiber-reinforced plastic or the like that possesses a sufficient rigidity, can be used. The upper plate part naturally also can be made from such a material.

In another embodiment the adapter is substantially planar on the top side in order to be able to support the patient positioning plate. In contrast to the previously specified embodiment, it can be attached on the underside by at least two projecting sections on the diagnosis and/or treatment table. Thus no large-area, curved positioning surface is-present, but instead a quasi-punctiform positioning surface is present in the form of at least two support-like sections that project from the lower table. The sections can be fashioned as one piece with the upper plate part or alternatively, can be fashioned as separate elements attached to the upper plate part.

In a further exemplary embodiment of the adapter it has a substantially U-shaped curved plate component with edge sections that are substantially planar and with a top side serving to accept the patient positioning plate, while the underside of the center sections cooperates with the diagnosis and/or treatment table. This U-shaped adapter is appropriately formed as a vacuum-drawn plate component, such that it can be very precisely adapted to the trough shape of the table in terms of its U-shape. In combination with the implementation of the attachment elements in the form of Velcro® strips, this embodiment represents the simplest adapter shape, but it is particularly advantageous both in terms of production and in terms of use since it is a one-piece formed part that is relatively simple to produce; and it is a light component that can be positioned by anyone without assistance. Also, since it is a narrow element, so no storage difficulties result.

In another embodiment of the adapter is formed as a planar plate with the attachment elements at the sides thereof, in particular plugs, catches or clamps that engage the diagnosis and/or treatment table on the sides and/or underside. This adapter is likewise very simply implemented and can likewise be positioned without problems. It merely has to be placed on the diagnosis and/or treatment table and attached with the plug, catch or clamp, It is even conceivable to implement the edge-side attachment element as Velcro® strips when corresponding Velcro® attachment elements are provided on the underside of the diagnosis and/or treatment table.

In a further embodiment of the inventive adapter, an anti-slip coating or covering is provided at the top side, to prevent any sliding in the direction of the longitudinal axis of the plate. For example, a rubber or foam rubber covering or a rubber coating can be used as such a covering.

In another embodiment of the invention, a deformable, in particular elastic, covering is provided on which for example, the Velcro® strips or the like can be arranged at the attachment area to the diagnosis and/or treatment table. This deformable, covering serves to compensate possible geometric differences between various table models and enables the adapter to be able to be attached to different table types despite of differences in shape, as long as these differences are not too great and can be accommodated by the deformable covering.

As described, the plate part or plate parts can be formed of a carbon fiber composite material or a plastic, preferably an epoxy resin. In principle x-ray transparent materials should be used that do not lead to any image artifacts in the exposure of x-ray images or the like, In addition to the adapter, the invention also concerns a patient transfer system having a transport cart or gurney with a patient positioning plate that can be removed or laterally slid therefrom, as well as an adapter as in any of the aforementioned embodiments. The patient positioning plate in particular should be vertically movable with a suitable lifting mechanism when it is to be laterally slid and not removed, such that it can be positioned sufficiently high in order to be able to be slid over the adapter and subsequently lowered.

DESCRIPTION OF THE PREFERRED EMBODIMENTS

Figure 1:
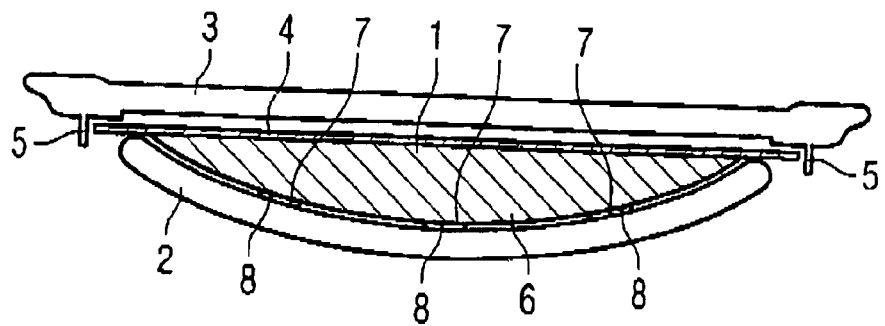
FIG. 1 shows an embodiment of an inventive adapter arranged on a diagnosis and/or treatment table and on which a patient positioning plate is accepted.

FIG. 1 shows an inventive adapter 1 that is received into the trough-shaped depression of a diagnosis and/or treatment table 2, for example of an x-ray system. A patient positioning plate 3 transferable from a patient transport cart is received on the adapter 1.

The adapter is formed of an upper plate part 4 that (in the exemplary embodiment) is planar, and thus is fashioned as a flat plate. The width of the plate part 4 is dimensioned such that side projections 5 of the patient positioning plate 3 overlap the plate part 4 on the edges with slight play. Sliding of the patient positioning plate 3 transverse to the longitudinal axis thus is prevented.

The adapter 1 also has a formed part 6, mounted under the plate part 4 that substantially corresponds to the shape of the top side of the diagnosis and/or treatment table 2, A large positioning surface thus can be achieved. For attachment, on the underside of the formed part 6 in the exemplary embodiment, attachment elements are mounted in the form of hook-and-loop (Velcro®) strips 7 that cooperate with corresponding Velcro® strips 8 that are normally already present on the top side of the diagnosis and/or treatment table, whereby the adapter 1 can be securely arranged.

The plate part 4 preferably is compared of a carbon fiber composite material, and the formed part 6 can be, for example, a foam formed part that is sufficiently stable.

Figure 2:
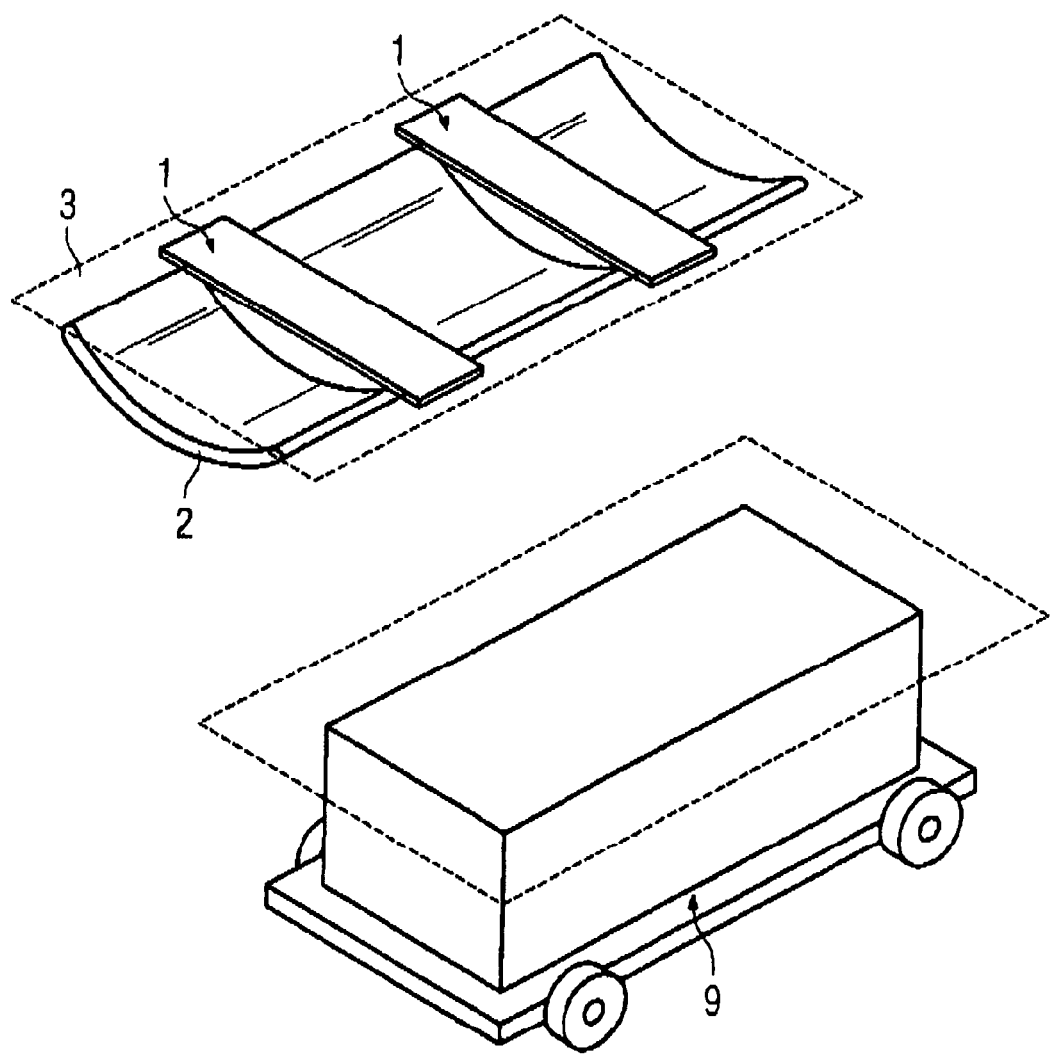
FIG. 2 is a schematic perspective view of the arrangement of FIG. 1, as well as showing a patient transport cart from which the patient positioning plate has been transferred.

FIG. 2 shows in perspective representation a complete patient transfer system including the arrangement from FIG. 1. In the exemplary embodiment, two adapters 1 are used, the first in the front area and the other in the back area of the diagnosis and/or treatment table 2. As specified, their width conforms to the separation of the two projections 5: their length can be, for example, 20 or 30 cm. Also shown dashed is the placed patient positioning plate 3 as well as the patient transport cart 9 from which the patient positioning plate 3 was transferred. For this transfer different embodiments are possible. The patient positioning plate 3 can be removed from the patient transport cart 9, meaning it can be raised. Attentively, the patient transport cart 9 can have a suitable lifting mechanism that enables vertical motion of the patient positioning plate 3. The patient positioning plate 3 itself preferably can be extracted transversely to the longitudinal axis of the patient transport cart 9, for which a corresponding extraction mechanism is provided. This enables the patient transport cart 9 to be positioned near the diagnosis and/or treatment table, and the patient positioning plate 3 then is raised, subsequently extracted to the side, and shifted over the diagnosis and/or treatment table 2 on which both adapters 1 are already arranged, whereupon it is lowered. The patient positioning plate 3 then can be detached from the extraction mechanism, so that it can be inserted into the transport cart 9 again and the cart 9 can be removed. Likewise, the patient positioning plate 3 can be received again on the extraction mechanism. FIG. 2 shows the inventive patient transfer system in the form of a basic illustration.

Figure 3:
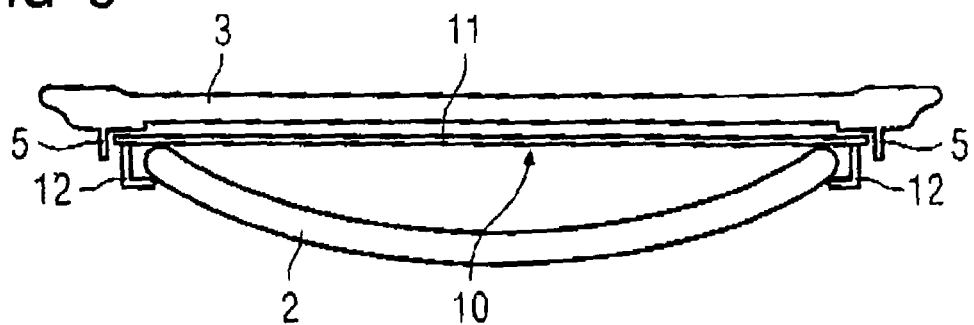
FIG. 3 shows a second embodiment of an adapter with edge-side attachment elements.

FIG. 3 shows a further inventive embodiment of an adapter 10. This also has a plate part 11 that is dimensioned in terms of Its shape or width corresponding to the separation of the projections 5. In the shown example, on the plate part 11 two-attachment elements are provided in the form of clamping arms or clamping jaws 12 that are arranged on the edges on the plate part 11 and can be pivoted downwardly. For attachment, the adapter 10 is placed on the side edges of the diagnosis and/or treatment table 2, whereupon the clamping jaws 12 are pivoted downwardly and engage the edge of the diagnosis and/or treatment table 2. They can be provided with a type of self-locking mechanism that prevents an unintentional release and ensures that they remain securely attached. It is also possible to provide a rubber overlay for preventing slippage and the like.

Figure 4:
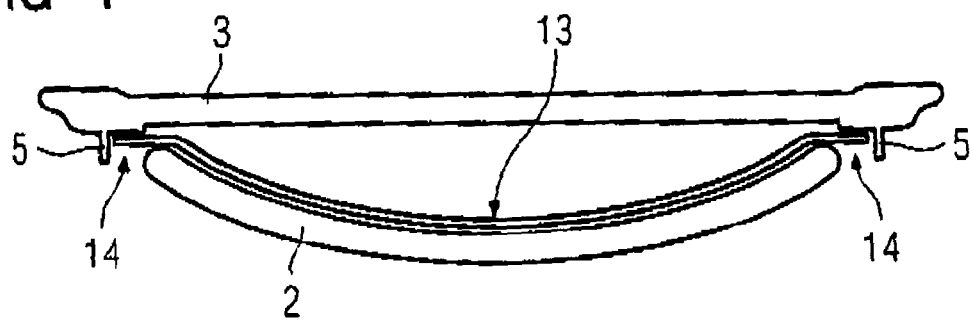
FIG. 4 shows a further embodiment of an inventive adapter as a one-piece U-shaped adapter.

FIG. 4 shows a further inventive embodiment of an adapter 13. This is a one-piece unit and preferably is formed as a plate part in a vacuum drawing method. The adapter 13 is substantially U-shaped and substantially corresponds in terms of its shape to the trough shape of the diagnosis and/or treatment table 2. Two horizontal sections 14 are provided on its edges, on the top of which the patient positioning table 3 is situated. The width of the adapter 13 is also dimensioned here corresponding to the separation of the projections 5. Particularly when projections should not be present at the patient positioning table 3, slippage is prevented by—as shown in FIG. 5—anti-slip coverings or coatings 16 (for example in the form of rod-like rubber coverings or the like) are provided on the top side of the horizontal sections 14, on which the patient positioning table 3 then rests.

Figure 5:
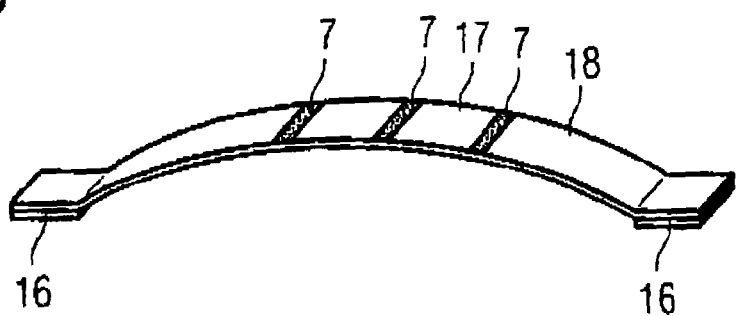
FIG. 5 is an underside view of the adapter of FIG. 4.

As FIG. 5 further shows, provided on the underside of the center section 17 (that is U-shaped) are the Velcro®D strips 7 as described in previous embodiments that cooperate with Velcro® strips (not shown) on the diagnosis and/or treatment table 2. In the shown exemplary embodiment according to FIG. 5, the Velcro® strips 7 are arranged on a deformable, preferably elastic covering (at the underside of the middle section 17) that serves to compensate slight shape differences among diagnosis and/or treatment tables of different types or different manufacturers. Instead of the arrangement of the Velcro® strips 7 in the longitudinal direction, it is naturally also possible to arrange these in the transverse direction or to attach a complete Velcro® mat, etc.

Figure 6:
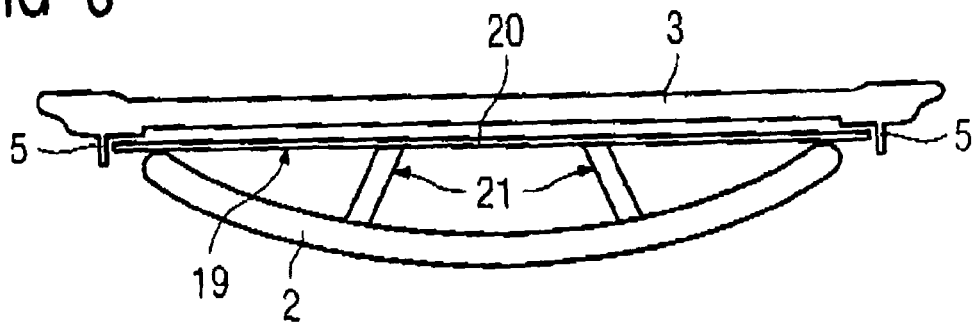
FIG. 6 shows a further embodiment of an adapter.

FIG. 6 shows a further embodiment of an adapter 19. This has a plate part 20 at the underside of which two support-like sections 21 are provided on which the adapter 19 rests on the diagnosis and/or treatment table 2. Corresponding Velcro® strips or the like can also be provided on the sections 19.

Common to all adapter embodiments is that the patient positioning plate of a patient transport cart is securely received and can be securely attached to a diagnosis and/or treatment table of an arbitrary medical examination modality, compensating for the shape differences with regard to the plate, such that the patient positioning plate ultimately forms the actual table plate on which the subsequent diagnosis or examination ensues, and the patient is not extensively transferred.

Although modifications and changes may be suggested by those skilled in the art, it is the intention of the inventor to embody within the patent warranted hereon all changes and modifications as reasonably and properly come within the scope of his contribution to the art.

I claim as my invention:

1. An adapter for attaching a patient positioning plate of a patient transport cart to a table for a medical procedure said table having a curved patient-receiving surface adapted for a patient to lie thereon, without said adapter, for said medical procedure, said patient positioning plate being removable from said patient transport cart and placeable on said table with said adapter between said patient positioning plate and said patient receiving surface of said table, said adapter comprising an adapter body, attachment elements carried by said adapter body for detachable attachment of the adapter body to said table, and said adapter body having a substantially flat top side configured to engage the patient positioning plate, said patient positioning plate having an underside and said top side of said adapter body substantially conforming to said underside of said patient positioning plate, and said adapter body having an underside with projections extending therefrom configured to engage said table at said curved patient-receiving surface of said table, and said projections having respective lengths substantially conforming to said curved patient-receiving surface.

2. An adapter as claimed in claim 1 wherein said top side of said adapter allows coupling with said patient positioning plate substantially without slippage.

3. An adapter as claimed in claim 1 wherein said adapter body is comprised of a material selected from the group consisting of carbon fiber composites, plastics and epoxy resins.

4. An adapter as claimed in claim 1 wherein said patient positioning plate has lateral projections, and wherein said adapter body has an attachment region for engaging said patient positioning plate, said attachment region being dimensioned so that said lateral projections overlap said adapter body with substantially no free motion.

5. An adapter as claimed in claim 1 wherein said attachment elements are selected from the group consisting of hook-and-loop strips and hook-and-loop pads.

6. An adapter as claimed in claim 1 wherein said attachment elements are selected from the group consisting of plugs, catches and clamps.

7. An adapter as claimed in claim 1 wherein said projections are formed as one-piece with said adapter body.

8. An adapter as claimed in claim 1 wherein said projections are separable from said adapter body.

9. An adapter as claimed in claim 1 wherein said adapter body comprises a flat plate having edges at which said attachment elements are disposed, said attachment elements being adapted to engage a portion of said table selected from the group consisting of table sides and an underside of said table.

10. An adapter as claimed in claim 1 comprising an anti-slip coating at said top side.

11. An adapter as claimed in claim 1 comprising an anti-slip covering at said top side.

12. An adapter as claimed in claim 1 comprising a deformable covering disposed at a region of said adapter body adapted for engaging said table.

13. A patient transfer system for use with a medical diagnosis/treatment table, said table having a patient-receiving surface adapted for a patient to lie thereon, without said adapter, for said medical procedure comprising:

a patient transport cart releasably carrying a patient positioning plate; and an adapter for attaching said patient positioning plate to said diagnosis/treatment table with said adapter between said patient positioning plate and said patient-receiving surface of said diagnosis/treatment table, said adapter comprising an adapter body, attachment elements carried on said adapter body for detachable attachment to said patient positioning plate, and said adapter body having a substantially flat top side conforming to an underside of said patient positioning plate, and said adapter body having an underside with projections extending therefrom configured to engage said table at said curved patient-receiving surface of said diagnosis/treatment table, and said projections having respective lengths substantially conforming to said curved patient-receiving surface.

\* \* \* \* \*